United States Patent [19]

Fischell et al.

[11] Patent Number: 5,167,644

[45] Date of Patent: Dec. 1, 1992

[54] MANUALLY SEALABLE INTRODUCER SHEATH

[76] Inventors: Robert E. Fischell, 14600 Viburnum Dr., Dayton, Md. 21036; Tim A. Fischell, 513 Cherry Ave., Los Altos, Calif. 94022

[21] Appl. No.: 656,591

[22] Filed: Feb. 19, 1991

[51] Int. Cl.⁵ .............................................. A61M 5/00
[52] U.S. Cl. ................................................... 604/264
[58] Field of Search .............. 604/256, 264, 167, 164, 604/171, 278, 51, 52, 53, 93, 265, 266, 267, 272

[56] References Cited

U.S. PATENT DOCUMENTS

| | | | |
|---|---|---|---|
| 3,058,472 | 10/1962 | Thornton, Jr. | 604/256 |
| 4,668,225 | 5/1987 | Russo et al. | 604/264 X |
| 4,730,616 | 3/1988 | Frisbie et al. | 604/164 X |
| 4,795,426 | 1/1989 | Jones | 604/256 X |
| 4,863,438 | 9/1989 | Gauderer et al. | 604/256 X |
| 4,944,732 | 7/1990 | Russo | 604/256 X |

*Primary Examiner*—John J. Wilson
*Assistant Examiner*—Jeffrey A. Smith

[57] ABSTRACT

A sheath for percutaneous insertion into an artery includes a manually insertable sealing tab having a flexible hinge molded onto the sheath near its proximal end. The tab includes a cylindrically shaped stopper that can be inserted into the sheath's proximal end to prevent blood loss when there is no catheter inserted into the sheath. The stopper design allows a guide wire to remain in place or be advanced or pulled out of the sheath when the stopper is in place to seal the sheath's proximal end.

4 Claims, 1 Drawing Sheet

MANUALLY SEALABLE INTRODUCER SHEATH

FIELD OF USE

This invention is in the field of percutaneous introducer sheaths that are inserted through a patient's skin in order to facilitate the entry of guide wires and catheters into a blood vessel.

BACKGROUND

Introducer sheaths are inserted percutaneously through the patient's skin, typically in the groin with their proximal end remaining outside the patient, and the distal end placed in an artery or vein. These sheaths include a deformable valve near their proximal end that is designed to seal a guide wire or catheter that is inserted through the sheath. The purpose of this seal is to prevent blood from leaking through the sheath. However, because the outside diameter of a guide wire is typically very much smaller than the outside diameter of the catheter that is inserted through the sheath, there is typically excessive blood leakage through the valve when the catheter is not in place.

SUMMARY OF THE INVENTION

The purpose of this invention is to overcome the problem of blood leakage when the catheter is not placed through the sheath. The invention consists of a sheath sealing tab that is molded onto the sheath's proximal end. The tab is joined to the sheath's proximal end by a hinge section formed from a thin flexible layer of plastic. At its center, the tab has a tapered stopper which has a maximum diameter approximately equal to the outside diameter of the catheter for which the sheath is designed. Outward from the stopper is a stiffened lift section having a greater thickness of plastic as compared to the hinge section.

When the catheter is removed from the sheath, the sheath's sealing tab is manipulated so that the tapered stopper is placed into the valve at the sheath's proximal end to prevent blood leakage. The design of the tab is such that, if there is a guide wire passing through the valve but no catheter, the guide wire is pushed aside by the tab. The guide wire can be advanced, pulled back or even removed entirely with the tab stopper in place in the valve without significant blood leakage.

DETAILED DESCRIPTION OF THE INVENTION

Figure 1:
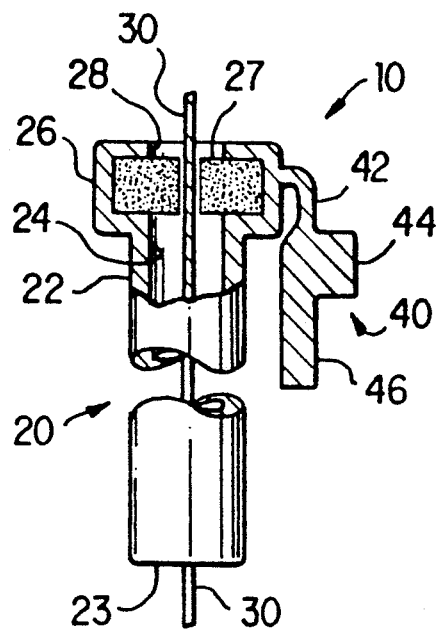
FIG. 1 is a partial longitudinal cross-sectional view of the manually sealable introducer sheath shown in the normal (unsealed) state.

FIG. 1 is a partial longitudinal cross-sectional view of the manually sealable introducer sheath 10 having a sheath sealing tab 40 attached near the proximal end of the sheath's main body 20, and through the sheath is passed a guide wire 30. The main body 20 consists of an elongated flexible tube 22 having a distal end 23 and, whose proximal end has a valve holder 26 which encloses a soft elastomer valve 27. The end of the holder 26 has an opening 28 which typically has the same inside diameter as the inside diameter of the interior passageway 24 of the tube 22.

In typical use, after the sheath 10 is percutaneously passed through the patient's skin so that its distal 23 end lies in a blood vessel, a catheter (not shown) whose outside diameter is just slightly smaller than the inside diameter of the passageway 24, is advanced over the guide wire 30 and through the sheath 10 into the blood vessel. When the sheath is in place, the valve 27, which is typically formed from foam rubber, seals tightly against the catheter's outer cylindrical surface. Thus, a tight seal is formed which prevents blood from leaking out the sheath's proximal end. However, when the catheter is not in place, the valve 27 does not seal tightly about the guide wire 30 so that considerable blood leakage can occur.

As shown in FIG. 1 the sealing tab 40 includes a hinge 42 that is molded onto the valve holder 26.

Figure 2:
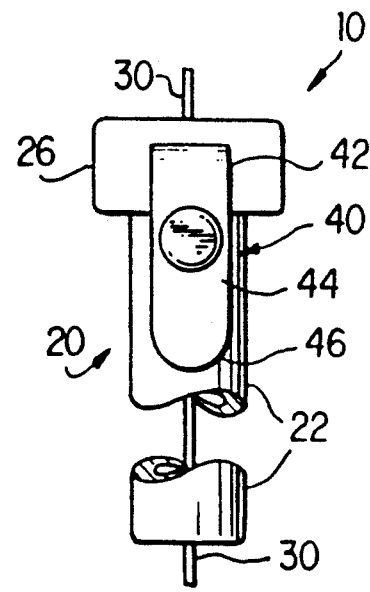
FIG. 2 is a side view of the proximal end of the sheath in the unsealed state.

At the center of the tab 40 is a tapered, generally cylindrical stopper 44 to which is molded a stiffened section 46. FIG. 2 is a side view of the sheath 10 which shows a flattened side 48 of the tab 40.

Figure 3:
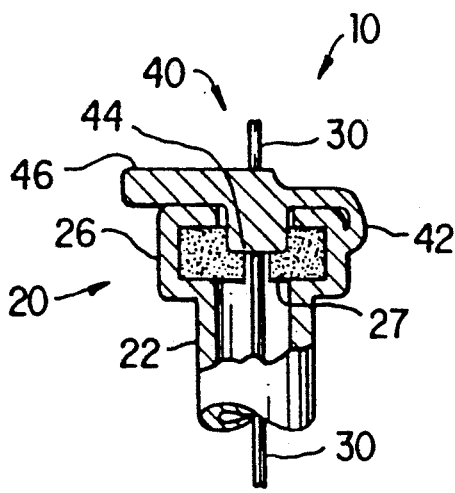
FIG. 3 is a partial cross-sectional view of the sheath shown in its sealed state.
Figure 4:
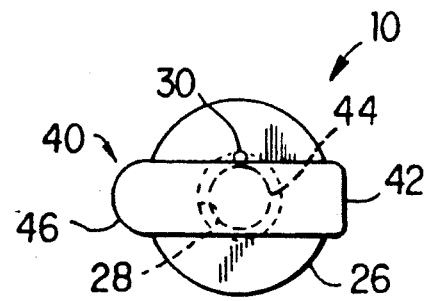
FIG. 4 is a top view of the sheath in the sealed state.

When there is no catheter inside the valve 27, the tab 40 can be manually moved by bending the flexible hinge 42 so that the stopper 44 is placed within the valve 27 as shown in FIG. 3. When this is done, the guide wire 30 is pushed to either one of the two flat sides 48 of the tab 40 as shown in FIG. 4. In this position, the sheath 10 is sealed so that there will not be significant blood leakage. This design still permits the guide wire 30 to be advanced, pulled back or even completely removed without significant blood leakage. If it is desired to reinsert the catheter, the thickened section 46 can be used to push the stopper 44 out of the valve 27. The preformed shape of the hinge 42 will then cause the tab 40 to return to its normal position as shown in FIG. 1.

The sheath 10 including the tab 40 would typically be molded from a plastic such as PVC, polyurethane, polyethylene or an equivalent elastomer material.

Figure 5:
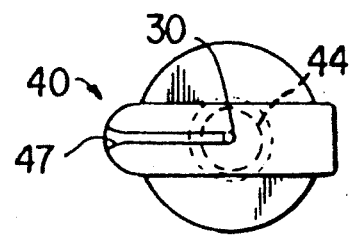
FIG. 5 is a top view of the sheath in the sealed state showing a slit for guide wire insertion into the sealing tab and stopper.

Although the design described herein is considered to be a preferred embodiment of the invention, it is also anticipated that the tab 40 may be extended perpendicularly from the holder 26 or the tab 40 could have a separate slit 47 as shown in FIG. 5 into which the guide wire 30 could be slipped. Another embodiment envisions a separate stopper which is not physically attached to the sheath but can be inserted into or pulled out of the valve 27.

Various other modifications, adaptations, and alternative designs are, of course possible in light of the above teachings. Therefore, it should be understood at this time that within the scope of the appended claims, the invention may be practiced otherwise than as specifically described herein.

What is claimed is:

1. A manually sealable introducer sheath for percutaneous insertion into a blood vessel of a human subject comprising:

an introducer sheath having a proximal end and a distal end and an elongated, generally cylindrical main body which has a sealing valve affixed to the main body near said proximal end and the main body having an essentially uniform outer diameter for most of the length of said main body said essentially uniform outer diameter extending to said distal end; and a manually insertable sheath sealing tab having a flexible hinge molded onto the sheath near said proximal end, the tab further having a generally cylindrical stopper which is releasably inserted into the sealing valve and wherein the sealing tab structure allows the passage of a guide wire to extend outward from said proximal end when the stopper is inserted into said sealing valve.

2. The introducer sheath as in claim 1 wherein the sheath sealing tab has a flat surface on at least one side.

3. The introducer sheath as in claim 1 in which the sheath sealing tab has a slit to accept a guide wire.

4. A manually sealable introducer sheath for percutaneous insertion into a blood vessel of a human subject comprising;

an introducer sheath having a proximal end and a distal end and an elongated, generally cylindrical main body, the main body having an essentially uniform outer diameter for most of the length of said main body said essentially uniform outer diameter extending to said distal end and having a sealing valve affixed to the main body near said proximal end; and a separate stopper which is releasably inserted into the sealing valve located near said proximal end which stopper prevents blood leakage while allowing a guide wire to be advanced or pulled back through the valve.

* * * * *